US011355237B2

(12) United States Patent
Vanderveen

(10) Patent No.: US 11,355,237 B2
(45) Date of Patent: Jun. 7, 2022

(54) OPIOID MANAGEMENT SYSTEM

(71) Applicant: CareFusion 303, Inc., San Diego, CA (US)

(72) Inventor: Timothy W. Vanderveen, Poway, CA (US)

(73) Assignee: CareFusion 303, Inc., San Diego, CA (US)

( * ) Notice: Subject to any disclaimer, the term of this patent is extended or adjusted under 35 U.S.C. 154(b) by 336 days.

(21) Appl. No.: 16/695,033

(22) Filed: Nov. 25, 2019

(65) Prior Publication Data

US 2020/0098474 A1    Mar. 26, 2020

Related U.S. Application Data

(63) Continuation of application No. 15/626,045, filed on Jun. 16, 2017, now Pat. No. 10,522,252.

(51) Int. Cl.
  *G16H 40/67* (2018.01)
  *G16H 20/17* (2018.01)
  (Continued)

(52) U.S. Cl.
  CPC .............. *G16H 40/67* (2018.01); *G16H 20/17* (2018.01); *G16H 40/20* (2018.01); *A61M 5/14* (2013.01);
  (Continued)

(58) Field of Classification Search
  CPC ............. G06F 19/3456; G06F 19/3462; G06F 19/3468; G06F 19/3418; G06F 19/322;
  (Continued)

(56) References Cited

U.S. PATENT DOCUMENTS 5,945,651 A    8/1999 Chorosinski et al.
6,650,964 B2   11/2003 Spano, Jr. et al.
(Continued)

FOREIGN PATENT DOCUMENTS

AU    2017 279 693 A1    1/2018
CA    2 636 115 C        6/2014
(Continued)

OTHER PUBLICATIONS

Yang, J., McAuley, J.J., & Leskovec, J. (2013). "Community Detection in Networks with Node Attributes." 2013 IEEE 13th International Conference on Data Mining, 1151-1156.
(Continued)

*Primary Examiner* — Manuel A Mendez
(74) *Attorney, Agent, or Firm* — Mintz Levin Cohn Ferris Glovsky and Popeo, P.C.

(57) ABSTRACT

A system may include a data processor and a memory storing instructions. The instructions may result in operations when executed by the data processor. The operations may include determining, based on location data from a positioning system, a presence of a cartridge at a location. The cartridge may include a substance. A quantity of the substance may be determined based on content data from a content meter at the location. Diversion of the substance may be detected based on the cartridge being present at the location and/or the quantity of the substance. Related methods and articles of manufacture, including apparatuses and computer program products, are also disclosed.

23 Claims, 5 Drawing Sheets

(51) Int. Cl.
*G16H 40/20* (2018.01)
*A61M 5/24* (2006.01)
*A61M 5/142* (2006.01)
*A61M 5/14* (2006.01)

(52) U.S. Cl.
CPC ..... *A61M 5/24* (2013.01); *A61M 2005/14208* (2013.01); *A61M 2205/3553* (2013.01); *A61M 2205/3561* (2013.01); *A61M 2205/50* (2013.01); *A61M 2205/6009* (2013.01); *A61M 2205/6054* (2013.01); *A61M 2205/6072* (2013.01)

(58) Field of Classification Search
CPC .... A61M 5/1723; A61M 5/172; A61M 5/142; A61M 5/14244; A61M 5/14276; A61M 5/14248; A61M 5/5086; A61M 5/20; G06Q 50/22; G06Q 50/24; G06Q 10/087; G06Q 10/10; G16H 20/13; G16H 20/10; G16H 20/17; A61J 7/0481; A61J 7/0076; A61J 7/0084; A61B 5/4839; G07F 17/0092
See application file for complete search history.

(56) References Cited

U.S. PATENT DOCUMENTS

| | | |
|---|---|---|
| 6,671,579 B2 | 12/2003 | Spano, Jr. et al. |
| 6,842,736 B1 | 1/2005 | Brzozowski |
| 6,868,344 B1 | 3/2005 | Nelson |
| 7,119,689 B2 | 10/2006 | Mallett et al. |
| 7,184,897 B2 | 2/2007 | Nelson |
| 7,275,645 B2 | 10/2007 | Mallett et al. |
| 7,303,081 B2 | 12/2007 | Mallett et al. |
| 7,311,207 B2 | 12/2007 | Mallett et al. |
| 7,318,529 B2 | 1/2008 | Mallett et al. |
| 7,562,025 B2 | 7/2009 | Mallett et al. |
| 8,147,479 B1 | 4/2012 | Wach et al. |
| 8,195,328 B2 | 6/2012 | Mallett et al. |
| 8,280,550 B2 | 10/2012 | Levy et al. |
| 8,319,669 B2 | 11/2012 | Weller |
| 8,357,114 B2 | 1/2013 | Poutiatine et al. |
| 8,595,021 B2 | 11/2013 | Mallett et al. |
| 8,606,596 B1 | 12/2013 | Bochenko et al. |
| 8,725,532 B1 | 5/2014 | Ringold |
| 8,738,177 B2 | 5/2014 | van Ooyen et al. |
| 8,768,724 B2 | 7/2014 | Whiddon et al. |
| 8,905,964 B2 | 12/2014 | Poutiatine et al. |
| 9,158,892 B2 | 10/2015 | Levy et al. |
| 9,202,052 B1 | 12/2015 | Fang et al. |
| 9,227,025 B2 | 1/2016 | Butterfield et al. |
| 9,354,178 B2 | 5/2016 | Lee |
| 9,427,520 B2 | 8/2016 | Batch et al. |
| 9,456,958 B2 | 10/2016 | Reddy et al. |
| 9,523,635 B2 | 12/2016 | Tilden |
| 9,636,273 B1 | 5/2017 | Harris |
| 9,752,935 B2 | 9/2017 | Marquardt et al. |
| 9,796,526 B2 | 10/2017 | Smith et al. |
| 9,817,850 B2 | 11/2017 | Dubbels et al. |
| 9,836,485 B2 | 12/2017 | Dubbels et al. |
| 9,842,196 B2 | 12/2017 | Utech et al. |
| 9,881,129 B1 | 1/2018 | Cave |
| 9,958,324 B1 | 5/2018 | Marquardt et al. |
| 10,032,344 B2 | 7/2018 | Nelson et al. |
| 10,101,269 B2 | 10/2018 | Judge et al. |
| 10,187,288 B2 | 1/2019 | Parker et al. |
| 10,209,176 B2 | 2/2019 | Proskurowski et al. |
| 10,241,038 B2 | 3/2019 | Nishimura et al. |
| 10,249,153 B2 | 4/2019 | Nelson et al. |
| 10,309,832 B2 | 6/2019 | Marquardt et al. |
| 10,345,242 B2 | 7/2019 | Zhao et al. |
| 10,832,207 B2 | 11/2020 | Vahlberg et al. |
| 2003/0158751 A1 | 8/2003 | Suresh et al. |
| 2008/0059226 A1 | 3/2008 | Melker et al. |
| 2008/0082360 A1 | 4/2008 | Bailey et al. |
| 2008/0140715 A1 | 6/2008 | Hakos |
| 2008/0288430 A1 | 11/2008 | Friedlander et al. |
| 2008/0306796 A1 | 12/2008 | Zimmerman et al. |
| 2008/0319795 A1 | 12/2008 | Poteet et al. |
| 2009/0160646 A1 | 6/2009 | Mackenzie et al. |
| 2011/0016110 A1 | 1/2011 | Egi et al. |
| 2011/0161108 A1 | 6/2011 | Miller et al. |
| 2012/0226447 A1 | 9/2012 | Nelson et al. |
| 2012/0265336 A1 | 10/2012 | Mallett et al. |
| 2012/0325330 A1 | 12/2012 | Prince et al. |
| 2013/0002429 A1 | 1/2013 | Johnson |
| 2013/0018356 A1 | 1/2013 | Prince et al. |
| 2013/0070090 A1 | 3/2013 | Bufalini et al. |
| 2013/0144254 A1 | 6/2013 | Amirouche et al. |
| 2013/0253700 A1 | 9/2013 | Carson et al. |
| 2013/0282392 A1 | 10/2013 | Wurm |
| 2013/0325727 A1 | 12/2013 | MacDonell et al. |
| 2014/0074284 A1 | 3/2014 | Czaplewski et al. |
| 2014/0149131 A1 | 5/2014 | Bear et al. |
| 2014/0249776 A1 | 9/2014 | King et al. |
| 2014/0277707 A1 | 9/2014 | Akdogan et al. |
| 2014/0375324 A1 | 12/2014 | Matsiev et al. |
| 2015/0038898 A1 | 2/2015 | Palmer et al. |
| 2015/0081324 A1 | 3/2015 | Adjaoute |
| 2015/0109437 A1 | 4/2015 | Yang et al. |
| 2015/0272825 A1 | 10/2015 | Lim et al. |
| 2015/0286783 A1 | 10/2015 | Kumar et al. |
| 2015/0323369 A1 | 11/2015 | Marquardt |
| 2015/0339456 A1 | 11/2015 | Sprintz |
| 2015/0362350 A1 | 12/2015 | Miller et al. |
| 2016/0034274 A1 | 2/2016 | Diao et al. |
| 2016/0062371 A1 | 3/2016 | Davidian et al. |
| 2016/0161705 A1 | 6/2016 | Marquardt et al. |
| 2016/0166766 A1 | 6/2016 | Schuster et al. |
| 2016/0283691 A1 | 9/2016 | Ali |
| 2017/0017760 A1 | 1/2017 | Freese et al. |
| 2017/0032102 A1 | 2/2017 | Skoda |
| 2017/0076065 A1 | 3/2017 | Darr et al. |
| 2017/0083681 A1 | 3/2017 | Sprintz et al. |
| 2017/0103203 A1 | 4/2017 | Sharma et al. |
| 2017/0108480 A1 | 4/2017 | Clark et al. |
| 2017/0109480 A1 | 4/2017 | Vahlberg |
| 2017/0109497 A1 | 4/2017 | Tribble et al. |
| 2017/0120035 A1 | 5/2017 | Butterfield et al. |
| 2018/0028408 A1 | 2/2018 | Li et al. |
| 2018/0039736 A1 | 2/2018 | Williams |
| 2018/0046651 A1 | 2/2018 | Dubbels et al. |
| 2018/0157803 A1 | 6/2018 | Mirov |
| 2018/0192942 A1 | 7/2018 | Clark et al. |
| 2018/0231415 A1 | 8/2018 | Marquardt et al. |
| 2018/0247703 A1 | 8/2018 | D'Amato |
| 2018/0259446 A1 | 9/2018 | Coffey et al. |
| 2018/0299375 A1 | 10/2018 | Young et al. |
| 2018/0330824 A1 | 11/2018 | Athey et al. |
| 2018/0365386 A1 | 12/2018 | Vanderveen |
| 2019/0088354 A1 | 3/2019 | Yanowitz et al. |
| 2019/0117883 A1 | 4/2019 | Abrams et al. |
| 2019/0247703 A1 | 8/2019 | Welde et al. |
| 2021/0308385 A1 | 10/2021 | Nisha et al. |

FOREIGN PATENT DOCUMENTS

| | | |
|---|---|---|
| CA | 2 848 274 C | 9/2016 |
| EP | 1 973 593 B1 | 4/2013 |
| EP | 1 593 076 B1 | 10/2019 |
| WO | WO-2006/034367 A2 | 3/2006 |
| WO | WO-2014/055925 A1 | 4/2014 |
| WO | WO-2015/187682 A1 | 12/2015 |

OTHER PUBLICATIONS

Benjamin, X.C. et al. (2012). "Visual identification of medicine boxes using features matching." *IEEE International Conference on Virtual Environments Human-Computer Interfaces and Measurement Systems (VECIMS) Proceedings*, 43-47. Doi: 10.1109/VECIMS. 2012.6273190.

(56) References Cited

OTHER PUBLICATIONS

Cakaloglu, T. (Nov. 1, 2017). "Medi-Deep: Deep control in a medication usage." *2017 IEEE International Conference of Bioinfomratice and Biomedicine (BIBM)*, 899-904. Doi: 10.1109/BIBM.2017.8217776.

Neuman, M.R. et al. (May 13, 2012), "Advances in Medical Devices and Medical Electronics," in Proceedings of the IEEE, vol. 100, no. Special Centennial Issue, pp. 1537-1550,doi: 10.1109/JPROC.2012.2190684.

Uniyal, D. et al. (Nov. 7, 2014), "Pervasive Healthcare—A Comprehensive Survey of Tools and Techniques," arXiv:1411.1821v1, 48 pages.

Yaniv, Z. et al. (Oct. 1, 2016). "The National Library of Medicine Pill Image Recognition Challenge: An Initial Report." *Oct. 2016 IEEE Applied Imagery Pattern Recognition Workshop, (AIPR)*, 1-9. Doi: 10.1109/AIPR.2016.8010584.

Zhan, A. et al. (Jan. 5, 2016) "High Frequency Remote Monitoring of Parkinson's Disease via Smartphone: Platform Overview and Medication Response Detection," Retrieved Apr. 29, 2021. 12 pages.

Qui et al. (2016) "A survey of machine learning for big data processing." *EURASIP Journal on Advances in Signal Processing*, Article No. 67, 16 pages.

OPIOID MANAGEMENT SYSTEM

This Application is a Continuation of application Ser. No. 15/626,045 filed on Jun. 16, 2017, now U.S. Pat. No. 10,522,252, entitled "OPIOID MANAGEMENT SYSTEM," the entire contents of this application is incorporated herein by reference in its entirety.

TECHNICAL FIELD

The subject matter described herein relates generally to the dispensation of pharmaceuticals and more specifically to a management system for injectable opioids.

BACKGROUND

Opioid pain medications, such as morphine, hydromorphone, and fentanyl, are typically administered in single doses by medical professionals via intramuscular injections. By contrast, patient-controlled analgesia pumps provide patients direct control over the delivery of opioid pain medications. A patient-controlled analgesia pump is a computerized pump that houses a reservoir of containing multiple doses of opioid pain medication and is connected directly to a patient's vein. The patient-controlled analgesia pump may be configured to deliver a constant flow of opioid pain medication to the patient. Alternatively and/or additionally, the patient-controlled analgesia pump may allow the patient to self-administer individual doses of opioid pain medication on an as-needed basis.

SUMMARY

Systems, methods, and articles of manufacture, including computer program products, are provided for detecting diversion of an opioid pain medication. In one aspect, there is provided a system. The system may include at least one data processor and at least one memory. The at least one memory may store instructions that result in operations when executed by the at least one data processor. The operations may include: determining, based on location data from a positioning system, a presence of a cartridge at a location, the cartridge including a substance; determining, based on content data from a content meter at the location, a quantity of the substance in the cartridge; and detecting, based on the cartridge being present at the location and/or the quantity, a diversion of the substance included in the cartridge.

In some variations, one or more features disclosed herein including the following features can optionally be included in any feasible combination. The quantity may be determined by at least measuring, by the content meter, a volume of a liquid in the cartridge and/or a concentration of the substance in the liquid.

In some variations, the substance may be a controlled substance and/or an opioid pain medication.

In some variations, diversion may be detected based on the cartridge having been handled by an individual in response to determining that the individual is not authorized to handle the cartridge. The individual may not be authorized based on the individual not being associated with a patient who is prescribed the substance.

In some variations, an individual responsible for the diversion may be identified in response to detecting the diversion. The individual may be identified based on identification information. The individual may be identified by at least querying a database including a record. The record may indicate a time when the cartridge is checked into the location and/or checked out of the location. The record may further indicate that the individual checked the cartridge into location and/or checked the cartridge out of the location.

In some variations, diversion may be detected based on a travel time between the location and another location exceeding an expected travel time. The location may be a pump for delivering the substance from the cartridge to a patient. The other location may be a dispensation cabinet for storing the cartridge. Diversion may be detected based on a first quantity measurement performed when the cartridge is inserted into the pump being less than a second quantity measured when the cartridge is removed from the dispensation cabinet.

In some variations, diversion may be detected based on the location being a detour from an expected travel path of the cartridge.

In another aspect, there is provided a pump. The pump may include: a content meter configured to determine a quantity of a substance in a cartridge inserted into the pump; and a reader configured to determine identification information of an individual who inserted the cartridge into the pump and/or removed the cartridge from the pump. The pump may be configured to deliver the substance from the cartridge to a patient. The pump may further be configured to send, to a diversion controller, the quantity of the substance and/or the identification information of the individual. The quantity of the substance and/or the identification information of the individual may enable the diversion controller to detect a diversion of the substance.

In some variations, the content meter may include a flow meter, a gravimeter, and/or a refractometer. The pump may be a patient-controlled analgesic pump.

In another aspect, there is provided a method. The method may include: determining, by a content meter at a pump, a quantity of a substance in a cartridge inserted into the pump; determining, by a reader at the pump, identification information of an individual who inserted the cartridge into the pump and/or removed the cartridge from the pump; and sending, to a diversion controller, the quantity of the substance and/or the identification information of the individual, the quantity of the substance and/or the identification information of the individual enabling the diversion controller to detect a diversion of the substance.

In another aspect, there is provided a cartridge. The cartridge may include: a content meter configured to determine a quantity of a substance held in the cartridge; and a position tracker configured to determine a location of the cartridge. The cartridge may be configured to send, to a diversion controller, the quantity of the substance and/or the location of the cartridge. The quantity of the substance and/or the location of the cartridge may enable the diversion controller to detect a diversion of the substance.

In some variations, the apparatus may further include an identification tag including an identifier for the apparatus. The location of the apparatus may be further determined based on one or more scans of the identification tag.

In another aspect, there is provided a method. The method may include: determining, by a content meter at a cartridge, a quantity of a substance held in the cartridge; determining, by a position tracker at the cartridge, a location of the cartridge; and sending, to a diversion controller, the quantity of the substance and/or the location of the cartridge, the quantity of the substance and/or the location of the cartridge enabling the diversion controller to detect a diversion of the substance.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including, for example, to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to web application user interfaces, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
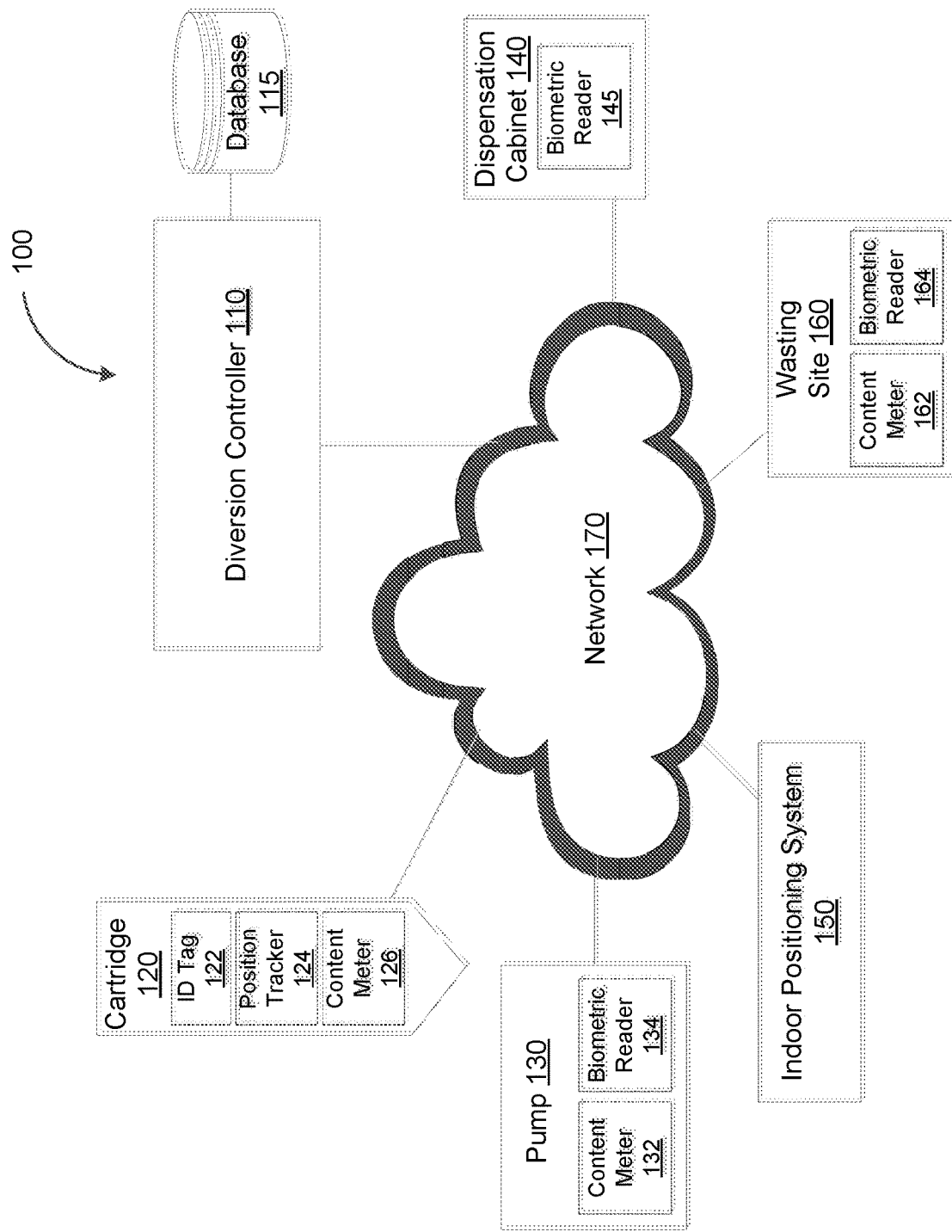
FIG. 1 depicts a system diagram illustrating a opioid management system, in accordance with some example embodiments.

Patient-controlled analgesic pumps may allow patients to directly control the delivery of opioid pain medication instead of having to rely on medical professionals to administer the opioid pain medication via intramuscular injections. Unlike single-dose intramuscular injections administered by medical professionals, a patient-controlled analgesic pump includes a cartridge that typically contains more doses of opioid pain medication than is ultimately used by the patient. Given the high likelihood for surplus opioid pain medication and a lack sufficient custodial oversight over such cartridges, opioid pain medication dispensed via patient-controlled analgesic pumps may be especially susceptible to diversion. As used herein, diversion may refer to a transfer and/or an attempt to transfer a controlled substance, such as an opioid pain medication, to a third-party who is not legally authorized to receive, possess, and/or consume the controlled substance. For example, the third party may not be a patient having a valid prescription for the controlled substance. Diversion of an opioid pain medication may occur at any point in time including, for example, during the compounding, dispensation, administration, and/or wasting of the opioid pain medication.

Thus, in some example embodiments, an opioid management system may be configured to establish a custody chain for cartridges containing opioid pain medication. Diversion of opioid pain medication may be detected based on the custody chain for the opioid pain medication cartridges. Establishing the chain for cartridges containing opioid pain medication may reduce and/or eliminate opportunities for diversion.

In some example embodiments, the opioid management system may establish a custody chain for a cartridge of opioid pain medication by tracking the location the cartridge. For example, the custody chain may include location data indicative of the movement of the cartridge within a facility such as, for example, a pharmacy, compounding pharmacy, a hospital, and/or the like. The custody chain may further include location data indicative of the movement of the cartridge between facilities such as, for example, when the cartridge is transported from a compounding pharmacy to a hospital. Alternatively and/or additionally, the opioid management system may establish the custody chain for the cartridge by tracking the contents of the cartridge. For example, the custody chain may include data indicative of the quantity, such as volume and/or concentration, of opioid pain medication in the cartridge at various points during the compounding, dispensation, administration, and/or wasting of the opioid pain medication. Furthermore, the opioid management system may establish the custody chain for the cartridge by tracking the identities of the individuals handling the cartridge. For instance, the custody chain may include identification information such as, for example, biometric data, identification numbers, and/or passcodes, that identify one or more individuals who compounded, dispensed, administered, and/or disposed of the opioid pain medication in the cartridge. The opioid management system may detect diversion when the custody chain for the cartridge indicates anomalies with respect to the movement of the cartridge, the content of the cartridge, and/or the individuals who handled the cartridge.

For clarity and conciseness, various embodiments of the present disclosure are described with respect to opioids and/or opioid pain medications. However, it should be appreciated that various embodiments of the present disclosure may be applicable to other substances instead of, and/or in addition to, opioids and/or opioid pain medications.

FIG. 1 depicts a system diagram illustrating an opioid management system 100, in accordance with some example embodiments. The opioid management system 100 may include a diversion controller 110, a cartridge 120, a pump 130, a dispensation cabinet 140, an indoor positioning system 150, and a wasting site 160. The diversion controller 110, the cartridge 120, the pump 130, the dispensation cabinet 140, the indoor positioning system 150, and/or the wasting site 160 may be communicatively coupled via a network 170. The network 170 may be any wired and/or wireless network including, for example, a public land mobile network (PLMN), a local area network (LAN), a wide area network (WAN), the Internet, and/or the like.

The cartridge 120 may be configured to include an opioid pain medication such as morphine, hydromorphone, fentanyl, and/or the like. It should be appreciated that the cartridge 120 may be a syringe, a vial, an intravenous (IV) bag, and/or any other appropriate form factor. In some example embodiments, the cartridge 120 may be inserted into the pump 130, which may be a patient-controlled analgesic pump configured to deliver the opioid pain medication on demand to a patient via a direct connection to the patient's vein. However, the opioid pain medication in the cartridge 120 may be delivered via a different mechanism instead of and/or in addition to the pump 130.

The pump 130 may deliver a constant flow of the opioid pain medication and/or allow the patient to self-administer individual doses of the opioid pain medication. As noted, diversion of an opioid pain medication may occur at any point in time such as, for example, during the compounding, dispensation, administration, and/or wasting of the opioid pain medication. Thus, in some example embodiments, the diversion controller 110 may be configured to detect diversion of the opioid pain medication by establishing a custody chain for the cartridge 120. The diversion controller 110 may detect diversion when the custody chain for the cartridge 120 indicates one or more anomalies with respect to the movement of the cartridge 120, the content of the cartridge 120, and/or the individuals who handled the cartridge 120.

Figure 2:
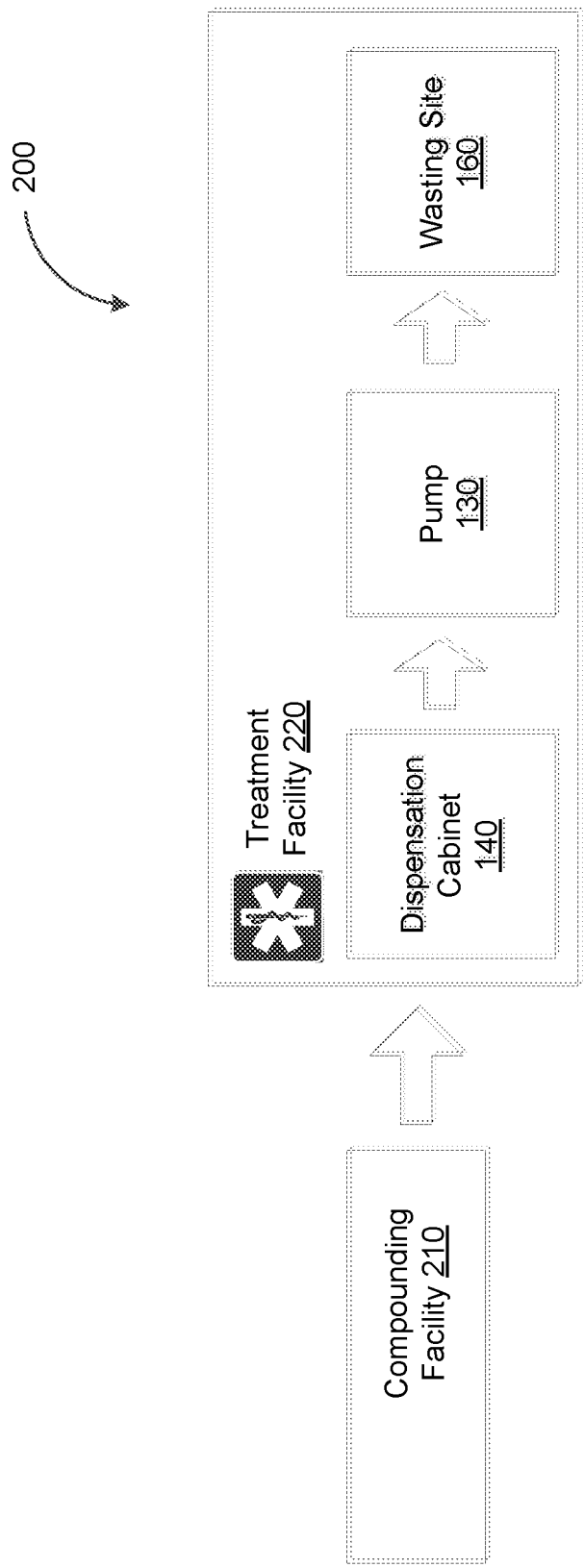
FIG. 2 depicts a flowchart illustrating a custody chain, in accordance with some example embodiments.

FIG. 2 depicts a flowchart illustrating a custody chain 200, in accordance with some example embodiments. Referring to FIGS. 1 and 2, the diversion controller 110 may track the cartridge 120 by establishing the custody chain 200. The custody chain 200 may include data indicative of the movement of the cartridge 120, the content of the cartridge 120, and/or the individuals who have handled the cartridge 120 during compounding, dispensation, administration, and/or wasting.

As shown in FIG. 2, the cartridge 120 may originate at a compounding facility 210 (e.g., a compounding pharmacy) where the cartridge 120 is filled with an opioid pain medication. The cartridge 120 may subsequently be transferred from the compounding facility 210 to a treatment facility 220 (e.g., a hospital). At the treatment facility 220, the cartridge 120 may initially be stored in the dispensation cabinet 140. Dispensing the opioid pain medication may include removing the cartridge 120 from the dispensation cabinet 140. The opioid pain medication may then be administered to a patient by inserting the cartridge 120 into the pump 130. It should be appreciated that the cartridge 120 may contain multiple doses (e.g., 30 to 150) of the opioid pain medication while only a portion of these doses may be delivered to the patient via the pump 130. Accordingly, when the cartridge 120 is removed from the pump 130, any doses of the opioid pain medication that remain in the cartridge 120 may be wasted at the wasting site 160. As used herein, wasting may refer to a procedure for disposing a controlled substance such as opioid pain medication. For instance, the procedure for wasting may be subject to state and/or federal regulations that require, for example, the presence of a witness.

Diversion of an opioid pain medication may occur at any point in time including, for example, during the compounding, dispensation, administration, and/or wasting of the opioid pain medication. For example, referring again to FIG. 2, diversion of the opioid pain medication may occur in the interim between when the cartridge 120 is removed from the dispensation cabinet 140 and when the cartridge 120 is inserted into the pump 130. Here, a portion of the opioid pain medication may be removed from the cartridge 120 and replaced by another substance that is visually indistinguishable from the opioid pain medication. Alternatively and/or additionally, diversion of the opioid pain medication may occur after the cartridge 120 is removed from the pump 130. The doses of the opioid pain medication remaining in the cartridge 120 may be diverted instead of being properly wasted at the wasting site 160. Thus, according to some example embodiments, the diversion controller 110 may detect diversion based on the custody chain 200. In particular, the diversion controller 110 may detect diversion when the custody chain 200 include any anomalies with respect to the movement of the cartridge 120, the contents of the cartridge 120, and/or the individuals who handled the cartridge 120.

As noted, the custody chain 200 may include data indicative of the movement of the cartridge 120 during the compounding, dispensation, administration, and/or wasting of the opioid pain medication contained in the cartridge 120. The cartridge 120 may be tracked using an identification tag 122 included with the cartridge 120. For example, the identification tag 122 may be, for example, a barcode, a quick response (QR) code, a radio frequency identification (RFID) tag, and/or the like. The identification tag 122 may store data that uniquely identifies the cartridge 120. Furthermore, the identification tag 122 may store data identifying the patient who is prescribed the opioid pain medication contained in the cartridge 120. In some example embodiments, the identification tag 122 may be scanned and/or tracked at various points during the compounding, dispensation, administration, and/or wasting of the opioid pain medication contained in the cartridge 120. Scanning the identification tag 122 may generate a digital record that becomes a part of the custody chain 200 for the cartridge 120. For instance, this record may indicate when and where the identification tag 122 is scanned. The record may also indicate one or more actions taken with respect to the cartridge 120 such as, for example, whether the cartridge is being checked into a location and/or checked out of a location. Furthermore, the record may indicate the individual taking the action with respect to the cartridge 120. These records may reflect the movement of the cartridge 120 between two or more locations. It should be appreciated that the diversion controller 110 may store at least some of these records at a database 115 coupled with the diversion controller 110.

To illustrate, the identification tag 122 may be scanned when the cartridge 120 is placed into and/or removed from the dispensation cabinet 140. Here, scanning the identification tag 122 may generate a record indicating a checkout of the cartridge 120 from the dispensation cabinet 140 at a first time $t_1$. The identification tag 122 may also be scanned when the cartridge 120 is inserted into the pump 130. Scanning the identification tag 122 here may generate a different record indicating a checkin of the cartridge 120 at the pump 130 at a second time $t_2$. Similarly, the identification tag 122 may be scanned when the cartridge 120 is removed from the pump 130. Scanning the identification tag 122 here may generate a record indicating a checkout of the cartridge 120 at the pump 130 at a third time $t_3$. Furthermore, the identification tag 122 may be scanned when any remaining doses of the opioid pain medication is wasted at the wasting site 160. Scanning the identification tag 122 here may generate a record indicating the cartridge 120 being checked in at the wasting site 160 at a fourth time $t_4$.

It should be appreciated that these records may include identification information for the one or more individual handling the cartridge 120 at each of the first time $t_1$, the second time $t_2$, the third time $t_3$, and/or the fourth time $t_4$. This identification information may be provided when the identification tag 122 is scanned during a checkin and/or a checkout at the dispensation cabinet 140, the pump 130, and/or the wasting site 160. For example, along with scanning the identification tag 122, the individual handling the cartridge 120 at the time may also be required to input an identification number, a passcode, and/or biometric data that uniquely identify the individual. Based on this identification information, the diversion controller 110 may identify the one or more individuals who removed the cartridge 120 from the dispensation cabinet 140 at the first time $t_1$, inserted the cartridge 120 into the pump 130 at the second time $t_2$, removed the cartridge 120 from the pump 130 at the third time $t_3$, and/or wasted the remaining doses of opioid pain medication at the wasting site 160 at the fourth time $t_4$.

Alternatively and/or additionally, the movement of the cartridge 120 may also be tracked based on positioning system coordinates of the cartridge 120 including, for example, global positioning system (GPS) coordinates and/or indoor positioning coordinates. In addition to and/or instead of the identification tag 122, the cartridge 120 may also include a position tracker 124. The position tracker 124 may be configured to determine one or more global positioning system coordinates of the cartridge 120. These global positioning system coordinates may be part of the custody chain 200 and may enable the diversion controller 110 to track the movement of the cartridge 120 between facilities such as, for example, when the cartridge 120 is transferred from the compounding facility 210 to the treatment facility 220. It should be appreciated that the indoor movements of the cartridge 120 (e.g., within a facility) may not be tracked based on global positioning system coordinates. As such, the position tracker 124 may be configured to interact with the indoor positioning system 150 to generate indoor positioning coordinates for the cartridge 120. The indoor positioning coordinates may also be part of the custody chain 200 and may enable the diversion controller 110 to track the movement of the cartridge 120 within a facility such as, for example, the compounding facility 210 and/or the treatment facility 220. At least some of the global positioning system coordinates and/or indoor positioning coordinates tracking the movement of the cartridge 120 may be stored at the database 115.

In some example embodiments, the indoor positioning system 150 may include a plurality of sensors deployed around the interiors of a facility such as, for example, the compounding facility 210 and/or the treatment facility 220. The sensors may be configured to detect a signal emitted by the position tracker 124. It should be appreciated that the position tracker 124 may interact with the indoor positioning system 150 using any wireless technology including, for example, radio frequency identification (RFID), near-field communication (NFC), magnetic field, Wi-Fi, acoustic signal, and/or the like. The strength and/or the orientation of the signal detected at the sensors may enable the indoor positioning system 150 to generate one or more indoor positioning coordinates indicative of the location of the cartridge 120 within a facility such as, for example, the compounding facility 210 and/or the treatment facility 220.

Figure 3:
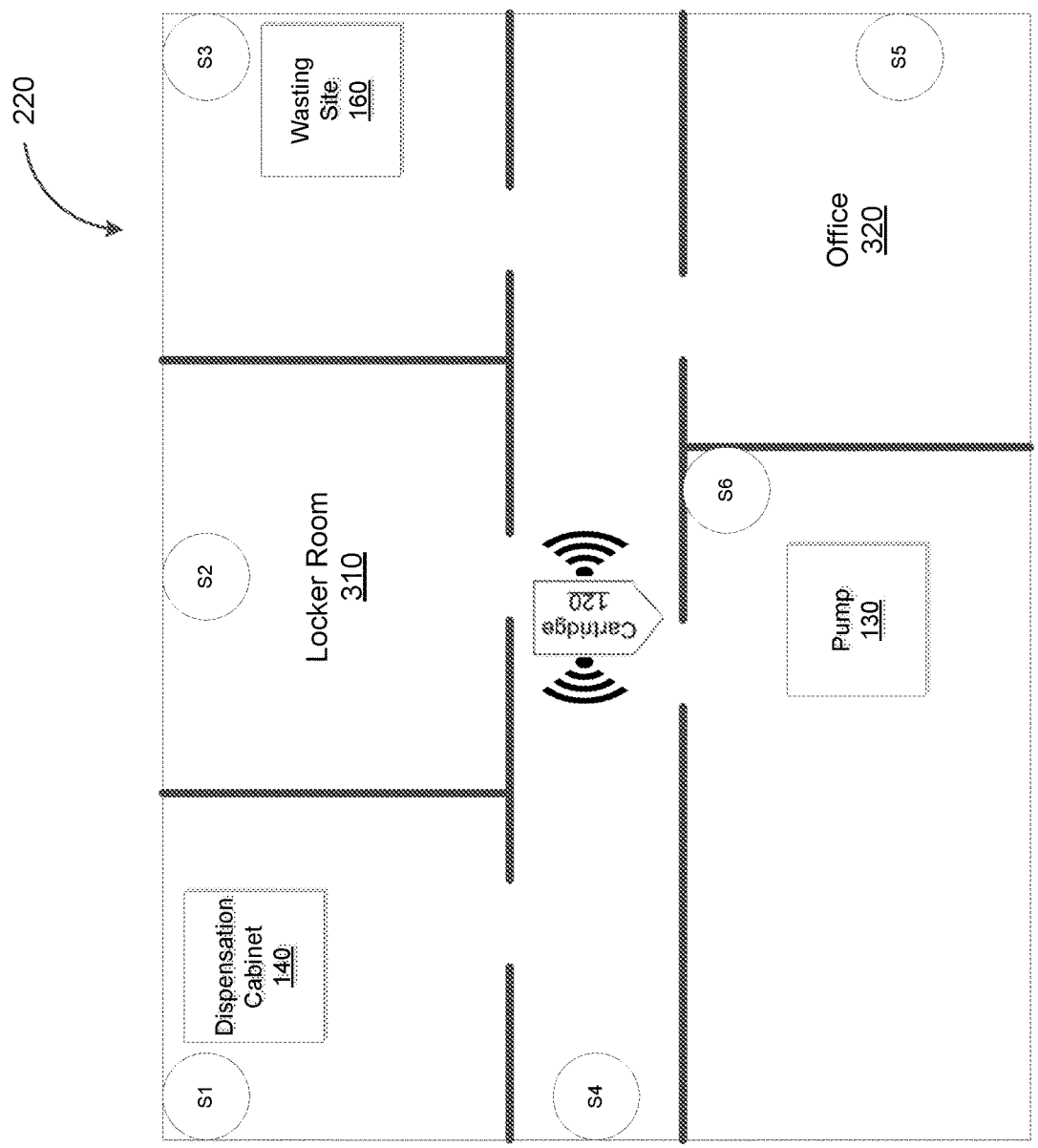
FIG. 3 depicts a block diagram illustrating a deployment of an indoor positioning system, in accordance with some example embodiments.

To further illustrate, FIG. 3 depicts a block diagram illustrating a deployment of the indoor positioning system 150, in accordance with some example embodiments. Referring to FIGS. 1-3, the indoor positioning system 150 may be deployed at the treatment facility 220. For example, as shown in FIG. 3, the indoor positioning system 150 may include a plurality of sensors including, for example, a first sensor $S_1$, a second sensor $S_2$, a third sensor $S_3$, a fourth sensor $S_4$, a fifth sensor $S_5$, and a sixth sensor $S_6$. As shown in FIG. 3, these sensors may be deployed at different areas around the treatment facility 220 such as, for example, near the dispensation cabinet 140, the pump 130, and/or the wasting site 160. In some example embodiments, the position tracker 124 may send a periodic polling signal that includes a unique identifier associated with the cartridge 120. Meanwhile, the sensors may be configured to detect the polling signals emitted by the cartridge 120 as the cartridge 120 moves around within the treatment facility 220. The indoor positioning system 150 may determine one or more indoor positioning coordinates indicative of the location of the cartridge 120 within the treatment facility 220 based on a strength and/or an orientation of the signal detected at the first sensor $S_1$, the second sensor $S_2$, the third sensor $S_3$, the fourth sensor $S_4$, the fifth sensor $S_5$, and/or the sixth sensor $S_6$.

Data associated with the identification tag 122 and/or the position tracker 124 may enable the diversion controller 110 to track the movement of the cartridge 120 between one or more locations within the facility. For example, based on this data, the diversion controller 110 may determine that the cartridge 120 was at the dispensation cabinet 140 before being moved to the pump 130. The cartridge 120 may then move from the pump 130 to the wasting site 160. As noted earlier, the movement of the cartridge 120 between one or more locations within the treatment facility 220 may be part of the custody chain 200 of the cartridge 120. The diversion controller 110 may detect diversion based on the presence of any anomalies in this custody chain 200 including, for example, anomalies with respect to the movement of the cartridge 120 between two or more locations.

One example of an anomaly in the movement of the cartridge 120 may be an abnormally long travel time from one location to another location. For example, the diversion controller 110 may detect diversion if the travel time between two locations exceeds an expected travel time. Data indicative of the expected travel times between different locations within a facility (e.g., the compounding facility 210, the treatment facility 220) may be stored at the database 115. These expected travel times may be determined based on an average travel time between different locations. In some example embodiments, the travel time between two locations may correspond to a quantity of time that elapses between when the cartridge 120 is checked out of one location and when the cartridge 120 is subsequently checked into the next location. For instance, the diversion controller 110 may detect diversion when a quantity of elapsed time between when the cartridge 120 is removed from the dispensation cabinet 140 and when the cartridge 120 is inserted into the pump 130 exceeds a threshold value. That is, the diversion controller 110 may detect diversion if a difference between the first time $t_1$ and the second time $t_2$ exceeds the threshold value. Alternatively and/or additionally, the diversion controller 110 may detect diversion when a quantity of elapsed time between when the cartridge 120 is removed from the pump 130 and when the cartridge 120 arrived at the wasting site 160 exceeds the threshold value. Here, the diversion controller 110 may detect diversion if the difference between the third time $t_3$ and the fourth time $t_4$ exceeds the threshold value.

Another example of an anomaly in the movement of the cartridge 120 may be a detour in an expected travel path of the cartridge 120. In some example embodiments, the database 115 may store data indicative of one or more expected travel paths of the cartridge 120. For instance, the one or more expected travel path may be determined based on the shortest paths between different locations, the most frequently used paths between different locations, and/or any other paths stored in the database 115. The diversion controller 110 may detect diversion if the diversion controller 110 determines that the cartridge 120 has detoured from these expected travel paths. For example, the expected travel path for the cartridge 120 may include moving from the dispensation cabinet to the pump 130 then to the wasting site 160. A detour from this expected travel path may include the cartridge 120 being present at one or more locations that are not part of the expected travel path. For example, the diversion controller 110 may detect diversion if the cartridge 120 moves from the dispensation cabinet 140 to the locker room 310 and/or the office 320 instead of moving directly from the dispensation cabinet 140 to the pump 130. Alternately and/or additionally, a detour from the expected travel path may include the cartridge 120 moving to a location in the expected travel path in a different order than the order indicated by the expected travel path. To illustrate, the diversion controller 110 may detect diversion if the cartridge 120 moves from the dispensation cabinet 140 to the wasting site 160 instead of moving from the dispensation cabinet 140 to the pump 130.

The identification tag 122 associated with the cartridge 120 may provide data identifying the patient who is prescribed the opioid pain medication contained in the cartridge 120. The pump 130 may also be associated with this specific patient. Furthermore, this patient may be under the care of one or more specific medical professionals including, for example, physicians and/or nurses. Thus, the diversion controller 110 may detect diversion if the individual who removed the cartridge 120 from the dispensation cabinet 140 is not one of the medical professionals assigned to care for the patient associated with the cartridge 120. For example, as noted, this individual may be required to enter identification information such as, for example, biometric data, an identification number, and/or a passcode when removing the cartridge 120 from the dispensation cabinet 140. The diversion controller 110 may detect diversion of the identification information provided by the individual does not match the identification information associated with the medical professionals assigned to care for the patient associated with the cartridge 120. Alternatively and/or additionally, the diversion controller 110 may also detect diversion if the cartridge 120 is inserted into a different patient-controlled analgesic pump and not the pump 130 associated with the patient. It should be appreciated that data indicative of the associations between patients, cartridges, patient-controlled analgesic pumps, and/or medical professionals may be stored at the database 115. As such, the diversion controller 110 may query the database 115 in order to determine whether the cartridge 120 is being inserted into the proper patient-controlled analgesic pump and/or handled by the appropriate individuals.

In some example embodiments, the custody chain 200 may further include data indicative of the content of the cartridge 120 at various points during the compounding, dispensation, administration, and/or wasting of the opioid pain medication contained in the cartridge 120. Thus, referring again to FIG. 1, the opioid management system 100 may include a plurality of content meters including, for example, a first content meter 132, a second content meter 162, and a third content meter 126. The first content meter 132, the second content meter 162, and/or the third content meter 126 may be configured to determine the content of the cartridge 120 including, for example, a quantity of the opioid pain medication contained in the cartridge 120. As shown in FIG. 1, the first content meter 132 may be deployed at the pump 130 while the second content meter 162 may be deployed at the wasting site 160. Meanwhile, the third content meter 126 may be incorporated into the cartridge 120. It should be appreciated that the first content meter 132, the second content meter 162, and/or the third content meter 126 may be Internet-of-Things (IoT) devices capable of communicating with the diversion controller 110 via the network 170. For example, the first content meter 132, the second content meter 162, and/or the third content meter 126 may send, to the diversion controller 110, data indicative of the content of the cartridge 120 at various points in time. Furthermore, content meters such as the first content meter 132, the second content meter 162, and/or the third content meter 126 may be deployed at different and/or additional locations including, for example, the dispensation cabinet 140.

As expressed by Equation (1) below, the quantity (e.g., q grams) of opioid pain medication present in the cartridge 120 may be a product of a total volume of liquid (e.g., v milliliters) present in the cartridge 120 and a concentration (e.g., c grams per milliliter) of the opioid pain medication present in the cartridge 120.

$$q = v \times c \qquad (1)$$

In order to determine the quantity of opioid pain medication present in the cartridge 120 at various points in time, the first content meter 132, the second content meter 162, and/or the third content meter 126 may include a flow meter and/or a gravimeter configured to measure the volume of a liquid present in the cartridge 120. Furthermore, the first content meter 132, the second content meter 162, and/or the third content meter 126 may also include a refractometer configured to determine the concentration of opioid pain medication present in the cartridge 120. The volume of liquid present in the cartridge 120 and the concentration of opioid pain medication present in the cartridge 120 may be used to determine the quantity of opioid pain medication that is present in the cartridge 120 at any one point in time such as, for example, during compounding, administration, dispensation, and/or wasting. However, it should be appreciated that the first content meter 132, the second content meter 162, and/or the third content meter 126 may include different and/or additional mechanisms for determining the quantity, volume, and/or concentration of opioid pain medication in the cartridge 120.

The diversion controller 110 may detect diversion when the custody chain 200 indicates one or more anomalies with respect to the contents of the cartridge 120. In particular, the diversion controller 110 may detect diversion if the quantity of opioid pain medication present the cartridge 120 is inconsistent with the expected quantity of opioid pain medication at a particular location. For example, the third content meter 126 may determine a first quantity $q_1$ of opioid pain medication present in the cartridge 120 when the cartridge 120 is removed from the dispensation cabinet 140. Meanwhile, the first content meter 132 and/or the third content meter 126 may also determine a second quantity $q_2$ of the opioid pain medication present in the cartridge 120 when the cartridge 120 is inserted into the pump 130. The diversion controller 110 may detect diversion if the second quantity $q_2$ is less than the first quantity $q_1$. Alternatively and/or additionally, the first content meter 132 and/or the third content meter 126 may also determine a third quantity $q_3$ of the opioid pain medication present in the cartridge 120 when the cartridge 120 is inserted into the pump 130. The second content meter 162 and/or the third content meter 126 may determine a fourth quantity $q_4$ of the opioid pain medication wasted at the wasting site 160 from the cartridge 120. Here, the diversion controller 110 may detect diversion if the fourth quantity $q_4$ is less than the third quantity $q_3$.

In some example embodiments, the custody chain 200 may further include data indicative of the individuals who handled the cartridge 120 during compounding, dispensation, administration, and/or wasting. The individuals handling the cartridge 120 may be identified based on a variety of identification information, which these individuals may be required to provide at various points in time including, for example, during compounding, dispensation, administration, and/or wasting. For instance, as noted, the individuals handling the cartridge 120 may be required to provide identification numbers and/or passcodes, which may be entered via a keyboard and/or by scanning a keycard that provides this data via near-field communication, radio frequency identification, barcode, quick response code, and/or the like. Alternatively and/or additionally, the individuals handling the cartridge 120 may be required to provide on biometric data.

Referring again to FIG. 1, the opioid management system 100 may include one or more biometric readers including, for example, a first biometric reader 134, a second biometric meter 145, and a third biometric reader 164. It should be appreciated that the first biometric reader 134, the second biometric meter 145, and/or the third biometric reader 164 may implement any type of biometric authentication technology including, for example, facial recognition, fingerprint identification, iris scan, retina scan, signature analysis, voice analysis, and/or the like. As shown in FIG. 1, the first biometric reader 134 may be deployed at the pump 130, the second biometric reader 145 may be deployed at the dispensation cabinet 140, and the third biometric reader 164 may be deployed at the wasting site 160. However, biometric readers may be deployed at different and/or additional locations including, for example, the cartridge 120.

The diversion controller 110 may detect diversion when the custody chain 200 indicates one or more anomalies with respect to the individuals who handled the cartridge 120. These anomalies may include a change and/or inconsistency in the individuals who handled the cartridge 120 between two locations. As noted, the database 115 may store data indicative of the individuals who handled the cartridge 120 at various points in time including, for example, during compounding, dispensation, administration, and/or wasting. For instance, the database 115 may store records indicating the one or more individuals who removed the cartridge 120 from the dispensation cabinet 140, inserted the cartridge 120 into the pump 130, removed the cartridge 120 from the pump 130, and/or wasted the remaining doses of opioid pain medication at the wasting site 160. The diversion controller 110 may query the database 115 and detect diversion if the records at the database 115 indicate that the individual who removed the cartridge 120 from the dispensation cabinet 140 is different from the individual who subsequently inserted the cartridge 120 into the pump 130. Alternatively and/or additionally, the diversion controller 110 may detect diversion if the individual who removed the cartridge 120 from the pump 130 is different from the individual who disposed the cartridge 120 at the wasting site 160.

It should be appreciated that the diversion controller 110 may further use biometric data from the first biometric reader 134, the second biometric reader 145, and/or the third biometric reader 164 to identify one or more individuals who may be responsible for the diversion of the opioid medication contained in the cartridge 120. As noted earlier, the diversion controller 110 may detect diversion based on the presence of one or more anomalies in the movement of the cartridge 120, the content of the cartridge 120, and/or the individuals who handled the cartridge 120. In response to detecting the diversion, the diversion controller 110 may identify, based on the biometric data, one or more individuals who had previously handled the cartridge 120.

To further illustrate, the diversion controller 110 may detect diversion based on an anomaly in the movement of the cartridge 120 and/or the content of the cartridge 120. For example, the diversion controller 110 may detect diversion in response to detecting the cartridge 120 being present in an unauthorized location (e.g., the locker room 310) subsequent to being removed from the dispensation cabinet 140. As such, the diversion controller 110 may identify, based on biometric data from second biometric reader 145 at the dispensation cabinet 140, the individual who removed the cartridge 120 from the dispensation cabinet 140 as a possible perpetrator of the diversion.

Alternatively and/or additionally, the diversion controller 110 may detect diversion based on an inconsistency in the content of the cartridge 120, when the cartridge 120 is inserted into the pump 130. For example, the diversion controller 110 may detect diversion if the quantity of opioid pain medication present in the cartridge 120 when the cartridge 120 is inserted into the pump 130 is less than the quantity of opioid pain medication present in the cartridge 120 when the cartridge 120 is removed from the dispensation cabinet 140. In response to detecting this diversion, the diversion controller 110 may identify the individual who removed the cartridge 120 from the dispensation cabinet 140. The diversion controller 110 may further identify the individual who inserted the cartridge 120 into the pump 130. These individuals may be identified as possible perpetrators of the diversion. It should be appreciated that the diversion controller 110 may identify these individuals based on the identification information (e.g., biometric data, identification number, password, and/or the like) that is entered when the cartridge 120 is removed from the dispensation cabinet 140 and/or when the cartridge 120 is inserted into the pump 130. As noted, this identification information may be stored at the database 115. Thus, the diversion controller 110 may identify these individuals by at least querying the database 115.

According to some example embodiments, the diversion controller 110 may use identification information to track the behavior of various individuals over time. As noted, identification information may be entered when one or more individuals perform an action with respect to the cartridge 120 such as, for example, removing the cartridge 120 from the dispensation cabinet 140, inserting the cartridge 120 into the pump 130, removing the cartridge 120 from the pump 130, and/or wasting the remaining doses of opioid pain medication from the cartridge 120 at the wasting site 160. This identification information may include biometric data from the first biometric reader 134, the second biometric reader 145, and/or the third biometric reader 164. Alternatively and/or additionally, this identification information may include an identification number and/or a password input via a keyboard and/or by scanning a keycard. The diversion controller 110 may use this identification information to differentiate data corresponding to the behavior of various individuals over time. Furthermore, the diversion controller 110 may identify norms in the behavior of each single individual (e.g., Nurse A from the treatment center 220) as well as norms in behavior across one or more groups of individuals (e.g., all nurses at the treatment center 220). The diversion controller 110 may detect diversion if the diversion controller 110 identifies behavior that deviates from one or more of these norms.

Tracking the behavior of various individuals may include correlating, based on the biometric data, various types of data collected by the opioid management system 100. For example, based on the biometric data of Nurse A, the diversion controller 110 may track all instances of when Nurse A removed a cartridge, such as the cartridge 120, from the dispensation cabinet 140. The diversion controller 110 may further track, based on the biometric data of Nurse A, all corresponding instances of when Nurse A then inserted the cartridge into a patient-controlled analgesic pump, such as the pump 130. The diversion controller 110 may determine a norm for a quantity of time (e.g., x minutes) required for Nurse A to travel from the dispensation cabinet 140 to a patient-controlled analgesic pump such as the pump 130. Alternatively and/or additionally, the diversion controller 110 may determine a norm for Nurse A's travel speed (e.g., y meters per minute) from the dispensation cabinet 140 to a patient-controlled analgesic pump. The diversion controller 110 may detect diversion when Nurse A's travel time and/or travel speed between the dispensation cabinet 140 and a patient-controlled analgesic pump exceeds the norms for Nurse A. Alternatively and/or additionally, the diversion controller 110 may also detect diversion if Nurse A's travel time and/or travel speed exceeds the norms for all of the nurses at the treatment center 220.

In some example embodiments, the database 115 may store a plurality of other data that may be used by the diversion controller 110 when determining whether diversion has taken place. For example, the database 115 may store data tracking the movement of one or more individuals within a facility such as, for example, the compounding facility 210 and/or the treatment facility 220. To further illustrate, the movement of Nurse A may be tracked as Nurse A travels between the dispensation cabinet 140, the pump 130, the wasting site 160, the locker room 310, and/or the office 320. Here, the movement of Nurse A may be tracked based on signals emitted by a location tracker worn by Nurse A and/or by scanning a keycard upon entry to one or more locations. The diversion controller 110 may detect diversion if the data from the database 115 indicate that Nurse A spent an excessive amount of time in the locker room 310 and/or the office 320 between moving from the dispensation cabinet 140 to the pump 130 and/or from the pump 130 to the wasting site 160.

Alternatively and/or additionally, the database 115 may store event data indicating the occurrences of one or more events at the treatment facility 220 that may introduce deviation in the behavior of one or more individuals. For example, the database 155 may store event data indicating the occurrence of a medical emergency at the treatment facility 220 that may have delayed Nurse A's travel time and/or travel speed between the dispensation cabinet 140 and the pump 130. Alternatively and/or additionally, the database 115 may store scheduling data indicating the individuals staffing the treatment facility 220 at various times. This scheduling data may indicate a shift change, which may account for a discrepancy in the individuals who handled the cartridge 120. For instance, the diversion controller 110 may determine that Nurse A removed the cartridge 120 from the pump 130 but Nurse B wasted the remaining doses of opioid pain medication from the cartridge 120 at the wasting site 160. Here, the diversion controller 110 may detect diversion based on the discrepancy in the individuals who handled the cartridge 120 and the scheduling data from the database 115. As such, the diversion controller 110 may not detect diversion even though Nurse B wasted the remaining doses of opioid pain medication instead of Nurse A if scheduling data from the database 115 indicates a shift change from Nurse A to Nurse B. By contrast, the diversion controller 110 may detect diversion if the Nurse B wasted the remaining doses of opioid pain medication while the scheduling data from the database 115 indicate that Nurse A is still on duty.

Figure 4:
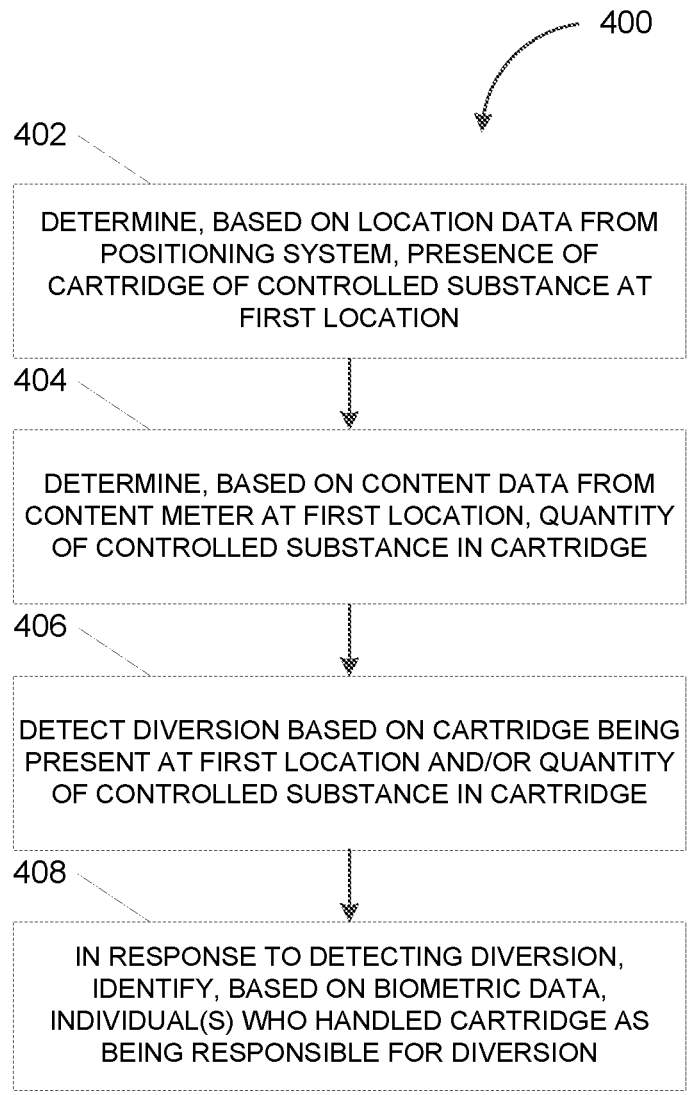
FIG. 4 depicts a flowchart illustrating a process for detecting diversion of an opioid pain medication, in accordance with some example embodiments.

FIG. 4 depicts a flowchart illustrating a process 400 for detecting diversion of an opioid pain medication, in accordance with some example embodiments. Referring to FIG. 4, the process 400 may be performed by the opioid management system 100.

At 402, the opioid management system 100 may determine, based at least on location data from positioning system, a presence of a cartridge of opioid pain medication at a location. In some example embodiments, the cartridge 120 may include the identification tag 122 and/or the position tracker 124, which enable the diversion controller 110 to track the movement of the cartridge 120 both within a facility (e.g., the compounding facility 210, the treatment facility 220) and/or between facilities. For example, the identification tag 122 may be scanned when the cartridge 120 is checked into and/or out of a location such as, for example, the dispensation cabinet 140, the pump 130, and/or the wasting site 160. Alternatively and/or additionally, the position tracker 124 may interact with the indoor positioning system 150 to generate location data indicative of the location of the cartridge 120 within the treatment center 220 such as, for example, at the dispensation cabinet 140, the pump 130, the wasting site 160, the locker room 310, and/or the office 320.

At 404, the opioid management system 100 may determine, based at least on content data from a content meter at the first location, a quantity of the opioid pain medication in the cartridge. In some example embodiments, the opioid management system 110 may include a plurality of content meters deployed at various locations. For instance, the first content meter 132 may be deployed at one location, such as the pump 130, to determine a volume of liquid and a concentration of opioid pain medication in the liquid present in the cartridge 120, when the cartridge 120 is inserted into and/or removed from the pump 130. Meanwhile, the second content meter 162 may be deployed at another location, such as the wasting site 160, to determine a volume of liquid and a concentration of opioid pain medication in the liquid wasted at the wasting site 160. Furthermore, the third content meter 126 may be included in the cartridge 120 and may be configured to determine a volume of liquid and a concentration of opioid pain medication in the liquid present in the cartridge 120. As noted, the diversion controller 110 may determine, based on the volume of liquid and the concentration of opioid pain medication in the liquid present in the cartridge 120, a quantity of opioid pain medication present in the cartridge 120. In doing so, the diversion controller 110 may track the quantity of opioid pain medication present in the cartridge 120 as the cartridge 120 is moved from the dispensation cabinet 140 to the pump 130 and to the wasting site 160.

At 406, the opioid management system 100 may detect diversion based on the cartridge being present at the first location and/or the quantity of the opioid pain medication in the cartridge. For example, the diversion controller 110 may detect diversion based on anomalies in the movement of the cartridge 120. For example, the diversion controller 110 may detect diversion if the cartridge 120 is present in an unauthorized location such as, for example, the locker room 310 and/or the office 320. Alternatively and/or additionally, the diversion controller 110 may detect diversion if the cartridge 120 detours between two or more authorized locations. For instance, after being removed from the dispensation cabinet 140, the cartridge 120 may detour to an authorized location such as the wasting site 160. Nevertheless, the detour may still represent an anomaly because moving directly to the wasting site 160 from the dispensation cabinet 140 is inconsistent with the requirement for the cartridge 120 to be transferred directly to the pump 130 after being removed from the dispensation cabinet 140.

Alternatively and/or additionally, the diversion controller 110 may also detect diversion if the content of the cartridge 120 is inconsistent with the expected content of the cartridge at a particular location. For example, the diversion controller 110 may detect diversion if content data from the first content meter 132 and/or the third content meter 126 indicate that the cartridge 120 contains less than an expected quantity of the opioid pain medication, when the cartridge 120 is inserted into the pump 130. Alternatively and/or additionally, the diversion controller 110 may detect diversion if the content data from the second content meter 162 and/or the third content meter 126 indicate that the quantity of the opioid pain medication wasted at the wasting site 160 is less than the quantity of the opioid pain medication remaining in the cartridge 120, when the cartridge 120 is removed from the pump 130.

At 408, the opioid management system 100 may identify, based on identification information, at least one individual who handled the cartridge as being responsible for the diversion. In some example embodiments, in response to detecting diversion, the diversion controller 110 may identify, based on identification information, one or more individuals who had previously handled the cartridge 120. As noted, the diversion controller 110 may detect diversion based on an anomaly in the movement of the cartridge 120, the content of the cartridge 120, and/or the individuals who handled the cartridge 120. Accordingly, if the diversion controller 110 determines that the cartridge 120 is present in an unauthorized location (e.g., the locker room 310) subsequent to being removed from the dispensation cabinet 140, the diversion controller 110 may identify, based on biometric data from the second biometric reader 145, the individual who removed the cartridge 120 from the dispensation cabinet 140 as being a possible perpetrator of the diversion. Alternatively and/or additionally, the diversion controller 110 may detect diversion due to an inconsistency in the content of the cartridge 120 when the cartridge 120 is inserted into the pump 130. Here, the diversion controller 110 may identify, based on biometric data from first biometric reader 134 and/or the second biometric reader 145, the individual who removed the cartridge 120 from the dispensation cabinet 140 and/or the individual who inserted the cartridge 120 into the pump 130. Alternatively and/or additionally, these individuals can be identified based on an identification number and/or a passcode entered via a keypad and/or by scanning a keycard. The diversion controller 110 may identify these individuals as being possible perpetrators of the diversion.

Figure 5:
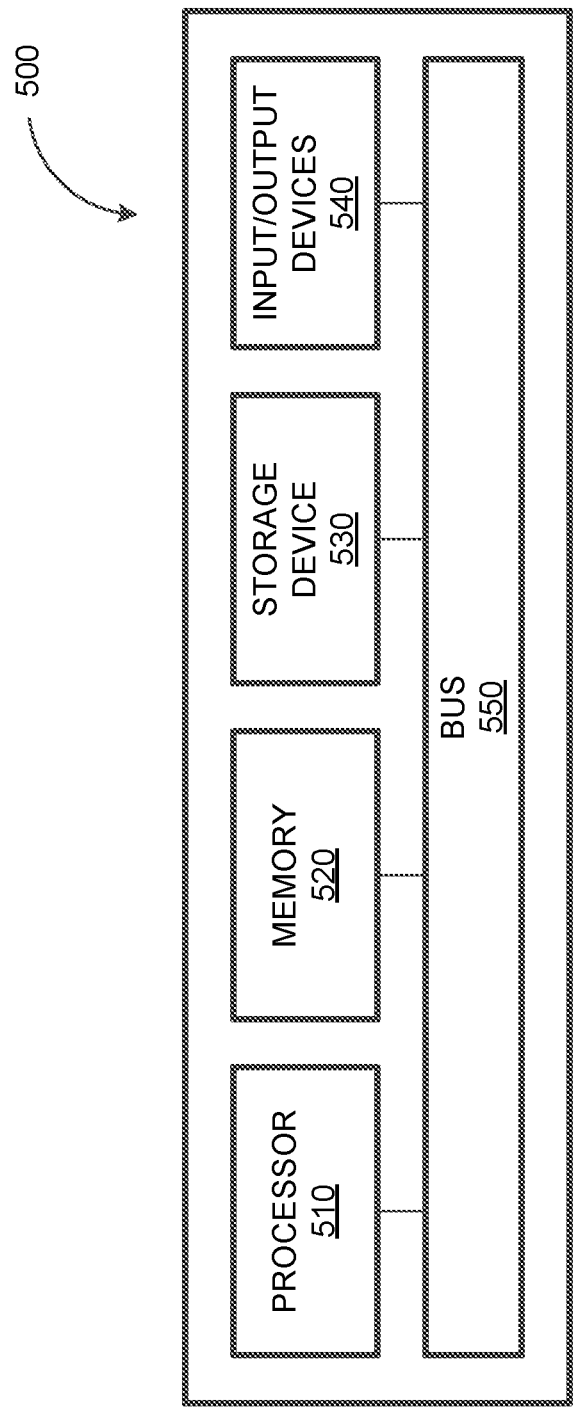
FIG. 5 depicts a block diagram illustrating a computing system, in accordance with some example embodiments.

FIG. 5 depicts a block diagram illustrating a computing system 500 consistent with implementations of the current subject matter. Referring to FIGS. 1 and 5, the computing system 500 can be used to implement the diversion controller 110 and/or any components therein.

As shown in FIG. 5, the computing system 500 can include a processor 510, a memory 520, a storage device 530, and input/output devices 540. The processor 510, the memory 520, the storage device 530, and the input/output devices 540 can be interconnected via a system bus 550. The processor 510 is capable of processing instructions for execution within the computing system 500. Such executed instructions can implement one or more components of, for example, the diversion controller 110. In some example embodiments, the processor 510 can be a single-threaded processor. Alternatively, the processor 510 can be a multi-threaded processor. The processor 510 is capable of processing instructions stored in the memory 520 and/or on the storage device 530 to display graphical information for a user interface provided via the input/output device 540.

The memory 520 is a computer readable medium such as volatile or non-volatile that stores information within the computing system 500. The memory 520 can store data structures representing configuration object databases, for example. The storage device 530 is capable of providing persistent storage for the computing system 500. The storage device 530 can be a floppy disk device, a hard disk device, an optical disk device, or a tape device, or other suitable persistent storage means. The input/output device 540 provides input/output operations for the computing system 500. In some example embodiments, the input/output device 540 includes a keyboard and/or pointing device. In various implementations, the input/output device 540 includes a display unit for displaying graphical user interfaces.

According to some example embodiments, the input/output device 540 can provide input/output operations for a network device. For example, the input/output device 540 can include Ethernet ports or other networking ports to communicate with one or more wired and/or wireless networks (e.g., a local area network (LAN), a wide area network (WAN), the Internet).

In some example embodiments, the computing system 500 can be used to execute various interactive computer software applications that can be used for organization, analysis and/or storage of data in various formats. Alternatively, the computing system 500 can be used to execute any type of software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 540. The user interface can be generated and presented to a user by the computing system 500 (e.g., on a computer screen monitor, etc.).

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system, comprising:
   at least one data processor; and
   at least one memory storing instructions which, when executed by the at least one data processor, result in operations comprising:
      detecting an event for a cartridge including a substance for a patient, wherein the event is one of a dispense event or a waste event for the cartridge;
      identifying an event location for the event based at least in part on a location of a device associated with the event;
      receiving, from a positioning system, a current patient location data identifying a current patient location of the patient, the current patient location data including an identifier for the current patient location;
      determining an expected travel time between the event location and the current patient location;
      receiving, from the positioning system, a current cartridge location data identifying a current cartridge location of the cartridge; and
      detecting a diversion of the substance, based at least in part on:
         (i) a first difference between: (a) the current cartridge location, and (b) the current patient location, and
         (ii) a second difference between: (a) a travel time from the event location to the current cartridge location, and (b) the expected travel time.

2. The system of claim 1, wherein the diversion of the substance is further detected based at least in part on a first quantity of the substance at the event location, a second quantity of the substance at the current cartridge location, and/or a third quantity of the substance at the current patient location.

3. The system of claim 2, wherein the first quantity, the second quantity, and/or the third quantity are determined by at least measuring a volume of a liquid in the cartridge and/or a concentration of the substance in the liquid.

4. The system of claim 1, wherein the diversion of the substance is further detected based at least in part on the current cartridge location deviating from an expected route between the event location and the current patient location.

5. The system of claim 1, wherein the diversion of the substance is further detected based at least in part on the cartridge being handled by an individual not authorized to handle the cartridge.

6. The system of claim 5, wherein the individual is determined to be not authorized to handle the cartridge based at least in part on the individual not being associated with the patient.

7. The system of claim 1, wherein the diversion of the substance is further detected based at least in part on the current cartridge location being an unauthorized location.

8. The system of claim 1, wherein the current patient location is determined based at least in part on a location of a pump associated with the patient, and wherein the identifier for the current patient location comprises an identifier associated with the pump.

9. The system of claim 8, wherein the first difference comprises a difference between the current cartridge location and the location of the pump associated with the patient.

10. The system of claim 1, wherein the second difference comprises a difference between the expected travel time and the travel time from a location of a dispensation cabinet storing the cartridge and the current cartridge location.

11. The system of claim 1, wherein the second difference comprises a difference between the expected travel time and the travel time from a wasting site for wasting unused substance remaining in the cartridge and the current cartridge location.

12. The system of claim 1, wherein the second difference comprises a difference between the expected travel time and the travel time from a wasting site for wasting unused substance remaining in the cartridge and the current cartridge location.

13. A computer-implemented method, comprising:
detecting an event for a cartridge including a substance for a patient, wherein the event is one of a dispense event or a waste event for the cartridge;
identifying an event location for the event based at least in part on a location of a device associated with the event;
receiving, from a positioning system, a current patient location data identifying a current patient location of the patient, the current patient location data including an identifier for the current patient location;
determining an expected travel time between the event location and the current patient location;
receiving, from the positioning system, a current cartridge location data identifying a current cartridge location of the cartridge; and
detecting a diversion of the substance, based at least in part on:
(i) a first difference between: (a) the current cartridge location, and (b) the current patient location, and
(ii) a second difference between: (a) a travel time from the event location to the current cartridge location, and (b) the expected travel time.

14. The system of claim 13, wherein the diversion of the substance is further detected based at least in part on a first quantity of the substance at the event location, a second quantity of the substance at the current cartridge location, and/or a third quantity of the substance at the current patient location.

15. The system of claim 14, wherein the first quantity, the second quantity, and/or the third quantity are determined by at least measuring a volume of a liquid in the cartridge and/or a concentration of the substance in the liquid.

16. The system of claim 13, wherein the diversion of the substance is further detected based at least in part on the current cartridge location deviating from an expected route between the event location and the current patient location.

17. The system of claim 13, wherein the diversion of the substance is further detected based at least in part on the cartridge being handled by an individual not authorized to handle the cartridge.

18. The system of claim 17, wherein the individual is determined to be not authorized to handle the cartridge based at least in part on the individual not being associated with the patient.

19. The system of claim 13, wherein the diversion of the substance is further detected based at least in part on the current cartridge location being an unauthorized location.

20. The system of claim 13, wherein the current patient location is determined based at least in part on a location of a pump associated with the patient, and wherein the identifier for the current patient location comprises an identifier associated with the pump.

21. The system of claim 20, wherein the first difference comprises a difference between the current cartridge location and the location of the pump associated with the patient.

22. The system of claim 13, wherein the second difference comprises a difference between the expected travel time and the travel time from a location of a dispensation cabinet storing the cartridge and the current cartridge location.

23. A non-transitory computer readable medium storing instructions, which when executed by at least one data processor, result in operations comprising:
detecting an event for a cartridge including a substance for a patient, wherein the event is one of a dispense event or a waste event for the cartridge;
identifying an event location for the event based at least in part on a location of a device associated with the event;
receiving, from a positioning system, a current patient location data identifying a current patient location of the patient, the current patient location data including an identifier for the current patient location;
determining an expected travel time between the event location and the current patient location;
receiving, from the positioning system, a current cartridge location data identifying a current cartridge location of the cartridge; and
detecting a diversion of the substance, based at least in part on:
(i) a first difference between: (a) the current cartridge location, and (b) the current patient location, and
(ii) a second difference between: (a) a travel time from the event location to the current cartridge location, and (b) the expected travel time.

* * * * *